United States Patent
Motoyuki et al.

[11] Patent Number: 6,121,501
[45] Date of Patent: *Sep. 19, 2000

[54] PROCESS FOR PREPARING 2,6-DIALKYLNAPHTHALENE

[75] Inventors: Masahiro Motoyuki, Osaka; Koji Yamamoto, Kobe, both of Japan; Ajit Vishwanath Sapre, Moorestown; John Paul Mc Williams, Woodbury, both of N.J.; Susan Patricia Donnelly, Kingwood, Tex.

[73] Assignees: Kabushiki Kaisha Kobe Seiko Sho, Kobe, Japan; Mobil Oil Corporation, Fairfax, Va.

[*] Notice: This patent is subject to a terminal disclaimer.

[21] Appl. No.: 09/288,847

[22] Filed: Apr. 9, 1999

Related U.S. Application Data

[63] Continuation-in-part of application No. 08/948,299, Oct. 10, 1997.

[51] Int. Cl.$^7$ .............................. C07C 1/00; C07C 4/12; C07C 5/22; C07C 2/68
[52] U.S. Cl. .................... 585/323; 585/312; 585/313; 585/314; 585/315; 585/486; 585/489; 585/478; 585/481; 585/449; 585/450; 585/467
[58] Field of Search ................. 585/323, 312, 585/313, 314, 315, 486, 489, 478, 481, 449, 450, 467

[56] References Cited

U.S. PATENT DOCUMENTS 4,950,824  8/1990  Shiroto et al. .
5,292,934  3/1994  Sikkenga et al. .
5,844,064  12/1998  Motoyuki et al. .

FOREIGN PATENT DOCUMENTS

WO 90/03961  4/1990  WIPO .

Primary Examiner—Walter D. Griffin
Assistant Examiner—Thuan D. Dang
Attorney, Agent, or Firm—Oblon, Spivak, McClelland, Maier & Neustadt, P.C.

[57] ABSTRACT

A process for producing 2,6-dialkylnaphthalene from a hydrocarbon feedstock that contains at least one component selected from the group consisting of dialkylnaphthalene isomers, monoalkylnaphthalene isomers, polyalkylnaphthalenes, and naphthalene, is provided that includes the following steps:

I. separating the hydrocarbon feedstock and/or a dealkylation product fed from step III into a naphthalene fraction, a monoalkylnaphthalene fraction, a dialkylnaphthalene fraction and a remaining products fraction;

II. separating and purifying 2,6-dialkylnaphthalene from the dialkylnaphthalene fraction of step I;

III. dealkylating the hydrocarbon feedstock and/or the remaining products fraction of step I and feeding the dealkylation product to step I; and IV. alkylating the naphthalene and monoalkylnaphthalene fractions of step I;

wherein the hydrocarbon feedstock is fed to step I or step III.

26 Claims, 9 Drawing Sheets

PROCESS FOR PREPARING 2,6-DIALKYLNAPHTHALENE

This application is a continuation in part of application Ser. No. 08/948,299 filed on Oct. 10, 1997.

BACKGROUND OF THE INVENTION

1. Field of the Invention

The present invention relates to a process for producing 2,6-dialkylnaphthalene (DAN) and, in particular, 2,6-dimethylnaphthylene (2,6-DMN) from a mixture which contains alkylnaphthalene or naphthalene.

2. Discussion of the Background

In the manufacture of high performance polyester resins such as polyethylene naphthalate polymer (PEN) or polybutyrene naphthalate polymer (PBN), 2,6-DMN is used as a precursor of 2,6-naphthalene dicarboxylic acid. This is because 2,6-DMN is easily oxidized to 2,6-naphthalene dicarboxylic acid, when compared to other precursors such as 2,6-diisopropylnaphthalene or 2-methyl-6-isobutyrylnaphthalenes. There are many applications for PEN, e.g., films and bottles, such as long time recording type video film, Advanced Photo System, hot fill containers, refillable bottles and tire codes. PEN has good physical properties in strength, thermal resistance and gas barrier properties. Typical PBN applications include electronics, insulators and car parts. PEN and PBN have heretofore been too expensive, however, to effectively expand their markets due to the limited commercially viable processes for producing 2,6-DMN.

There have been many proposals for preparing 2,6-DMN. U.S. Pat. No. 4,795,847 (Weitkamp et al.) describes a process for the preparation of 2,6-dialkylnaphthalene by alkylating naphthalene or 2-alkyl-naphthalene with an alkylating agent in the presence of a zeolite (specially ZSM-5) as a catalyst.

U.S. Pat. No. 5,001,295 (Angevine et al) describes a process for preparing DMN by using 2-monomethylnaphthalene (MMN) and naphthalene as a feedstock and a synthetic zeolite (MCM-22) as a catalyst, and it shows MCM-22 catalyst is more effective than ZSM-5 in alkylation of 2-MMN and naphthalene.

However, the above methods provide only unit operation (i.e batch) for alkylation of 2-MMN, which is an expensive feedstock and is not commercially available in a large amounts.

U.S. Pat. No. 4,990,717 (Sikkenga) and 5,073,670 (Sikkenga et al.) describe a multi-step process to produce 2,6-DMN from o-xylene and butadiene, which consists of;

1) preparation of 5-(o-tolyl)-pentene-2(OTP) by alkenylation of o-xylene with butadiene in the presence of a catalyst such as an alkali metal catalyst,
2) preparation of 1,5-dimethyltetralin (1,5-DMT) by cyclization of OTP in the presence of a catalyst such as platinum and copper on an ultra stable zeolite catalyst;
3) preparation of 1,5-dimethylnaphthalene (1,5-DMN) by dyhydrogenation of 1,5-DMT in the presence of a catalyst such as platinum and rhenium and gamma alumina; and
4) preparation of DMN mixture which is rich in the desirable 2,6-DMN, 1,6-DMN and 1,5-DMN by isomerization of 1,5-DMN in the presence of a catalyst such as a beta-zeolite catalyst.

If a process for separating 2,6-DMN from a DMN mixture were combined with the above steps, a complete process to produce purified 2,6-DMN could be provided.

As multiple steps complicate a process plant and increase the cost, it is not clear that the conventional processes could provide a process suitable for an economical preparation of purified 2,6-DMN.

In addition, it is very difficult to separate 2,6-DMN from other isomers by conventional separation methods such as distillation and cooling crystallization because;

1) There are very small differences in the boiling points of DMN isomers, and, in particular, between 2,6-DMN and 2,7-DMN wherein the difference in boiling points is only 0.3 C, and it is nearly impossible to separate 2,6-DMN by distillation.
2) The cooling of DMN isomer mixture solution of 2,6-DMN purification forms a precipitate of very fine 2,6-DMN crystals in suspension, and thus separation of the 2,6-DMN is extremely difficult.

Koide et al U.S. Pat. No. 4,992,619 reports a method for separating a methyl derivative of naphthalene from a mixture of materials in high purity by crystallization under pressure.

Moritoki et al U.S. Pat. No. 4,784,766 reports a pressure crystallization apparatus.

Accordingly, new and more efficient methods for commercially preparing dialkylnaphthalenes are sought.

SUMMARY OF THE INVENTION

According to one object of the invention, a method of preparing 2,6-dialkylnaphthalene is provided.

According to another object of the invention, a method of preparing 2,6-dimethylnaphthalene is provided.

These and other objects of the present invention are made possible by a process for producing 2,6-dialkylnaphthalene from a feedstock including hydrocarbons which contains at least one component selected from the group consisting of dialkylnaphthalene isomers, monoalkylnaphthalene isomers, polyalkylnaphthalenes, and naphthalene including the following steps:

I. separating the feedstock and/or a product fed from step III into a fraction containing naphthalene, a fraction containing monoalkylnaphthalene, a fraction containing dialkylnaphthalene and a fraction containing remaining products;

II. separating and purifying 2,6-dialkylnaphthalene from the dialkylnaphthalene fraction of step I;

III. dealkylating the feedstock and/or the fraction containing the remaining products of step I and feeding the product of dealkylation to step I;

IV. alkylating the fractions containing naphthalene and monoalkylnaphthalene of step I, wherein the feedstock is fed to step I or step III.

DESCRIPTION OF THE PREFERRED EMBODIMENTS

A more complete appreciation of the invention and many of the attendant advantages thereof will be readily obtained as the same becomes better understood by reference to the following detailed description when considered in connection with the accompanying drawings, which is not intended to be limiting unless otherwise specified.

Preferably, the present invention may be applied to any feedstock of hydrocarbons that contains alkylnaphthalenes such as naphthalene, MMN (monomethylnaphthalene) and DMN isomers. The present invention provides an effective production process of 2,6-dialkylnaphthalene (DAN), in particular, 2,6-dimethylnaphthalene (DMN) as high-value added product by utilizing a non-valuable feedstock.

In particular, LCO (Light Cycle Oil) and/or its heart cut fraction from FCC (Fluid Catalyst Cracking) or HC (Hydrocracker) is a preferable example of a feedstock. Although such feedstock usually contains alkylnaphthalenes at about 20 to 45 weight % of the feed stream, it has the following problems and difficulties for further processing:

1) Co-boilers

For example, LCO usually contains many components such as light paraffins and mono-aromatics with long chain alkyl-groups, which have similar boiling points to naphthalene, MMN and DMN (Co-boilers). It is very hard to separate alkylnaphthalenes from their co-boilers by distillation alone for further processing such as an alkylation step.

Therefore, if untreated, the co-boilers reduce the efficiency of the reactors. In the worst case, the co-boilers accumulate in the recycling streams in the process.

2) Polyalkylnaphthalenes (PAN)

PANs such as tri-methylnaphthalenes, isopropylnaphthalenes and tetramethylnaphthalenes are usually contained in the feed stream at about 10 to 20 weight % of the feed stream, i.e., almost one third to one half of the alkylnaphthalene contents. PAN is also produced at other process steps such as alkylation and isomerization as by-products. In the conventional art, no effective process to utilize PANs for the production of 2,6-dialkylnaphthalene has been proposed.

3) Sulfur and Nitrogen Compounds

The feed stream contains sulfur and nitrogen compounds, which might poison the catalyst for alkylation and isomerization, and these compounds should be excluded from the recycling streams and products.

The inventors have found that dealkylation (DA), especially hydrodealkylation (HDA) is (i) effective not only for cracking and/or reforming the co-boilers to lighter fractions, which results in much easier separation from naphthalenes, monoalkylnaphthalenes and dialkylnaphthalenes; but also, (ii) surprisingly effective for producing 2,6-dialkylnaphthalene especially 2,6-DMN by means of DA, especially HDA of polyalkylnaphthalenes (PAN) such as tri-methylnaphthalenes and heavier alkylnaphthalenes, which are contained in the feedstock and are also produced at alkylation step as useless by-products; and, (iii) effective for production of naphthalene and monoalkylnaphthalene which is suitable for alkylation feedstock.

The discovery results in more effective production of 2,6-DMN, not only at the alkylation step but also in the overall process because the invention provides an effective utilization of PAN.

Although a high feedstock conversion (e.g. Conversion of MMN) of around 50 to 60% provides a higher yield of 2,6-DMN, PAN production also increases, as shown in the TABLE 4 of the conventional processes, U.S. Pat. No. 5,744,670 (Motoyuki et al), the entire contents of which are hereby incorporated by reference. (DMN and PAN content after alkylation is 35% and 23% respectively at MMN conversion with 58.28%.). This causes naphthalene-ring loss and lower process yields if PAN is not utilized again in the recycled stream. Therefore, in order to minimize the loss, MMN conversion is limited to around 30% or so, which decreases 2,6-DMN yield.

As the present invention can provide the effective utilization (an additional production of 2,6-dialkylnaphthalene from DA of PAN) of PAN derived from the feedstock, and preferably from the feedstock and alkylation step, it allows much higher feedstock conversion at the alkylation step, of around 50% and greater, which also results in higher production of 2,6-dialkylnaphthalene. Further, the inventors found that 2,6-lean-dialkylnaphthalene as the remaining products of the purification of 2,6-dialkylnaphthalene can be dealkylated and changed to equilibrium distributions of dialkylnaphthalene isomers or 2,6-rich dialkylnaphthalene by producing naphthalene and monoalkylnaphthalene simultaneously.

Although the reaction mechanism of DA of 2,6-dialkylnaphthalene is believed to be completely different, the results and product composition of DA are similar to transalkylation and isomerization. This means that DA can take over the performance of transalkylation shown in the conventional processes, e.g., U.S. Pat. No. 5,744,670 effectively.

The present invention provides an effective production process for 2,6-dialkylnaphthalene as a high-value added product by utilizing a non-valuable feedstock.

As a preferable feedstock for the present process, any hydrocarbon feedstream containing alkylnaphthalenes including at least one component selected from the group consisting of dialkylnaphthalene isomers, monoalkylnaphthalene isomers, polyalkylnaphthalenes, and naphthalene, such as Light Cycle Oil (LCO) derived from Catalytically cracking petroleum oil may be used. Alternatively, as raw material, hydrocarbon feedstream such as LCO is pre-processed, and afterwards, its product is preferably used as a feedstock for the present process. The pre-processing preferably includes distillation (e.g. heart cutting), concentration, hydrotreating (HDT) to reform sulfur and nitrogen compounds, which are usually contained in feedstreams and which might poison the catalyst, de-sulfurization, de-nitrogenation and de-watering.

In the distillation and concentration as the pre-processing, it is preferable to separate light components such as monoaromatic compounds and non-aromatic light paraffins and heavy compounds such as tri-aroma and heavier compounds from alkylnaphthalene components.

The preferable conditions of HDT include a temperature of about 200 to 1,000° C., and more preferably 200 to 500° C., and a pressure of 0 to 250 atmospheres and preferably 5 to 50 atmospheres, a hydrogen circulation rate of from about 500 to 3,000 scf/bbl. The reaction is preferably accomplished utilizing a feed space velocity of about 0.1 to 10.0 $hr^{-1}$.

One preferred example of a suitable catalyst for HDT is an activated alumina supported catalyst bearing a Group VIII metal oxide and a Group VI-A metal oxide, preferably nickel and molybdenum respectively. The oxide may be preferably treated at 600–1200° F. in the presence of sulfur compounds.

The feedstock can be fed to the separation of step I and/or the dealkylation of step III. In the case that the feedstock is fed to step I, separating light components and heavy compounds from alkylnaphthalene components can be conducted in step I. On the other hand, in the case that the feedstock is fed to step III, PAN components in the feedstock can be reduced and changed to DMN or MMN components before separation of step I. In either case, effective production is obtained, since the remaining products of step I are fed to step III and the product of step III is fed to step I, as can be seen from FIG. 1.

For the separation of step 1, conventional techniques such as distillation may be used. In the case where the feed stream contains non-aromatic components having boiling points that are very similar to naphthalene and/or MMN, conventional solvent extraction techniques also can be applied in addition to the above mentioned distillation in step I.

Figure 1:
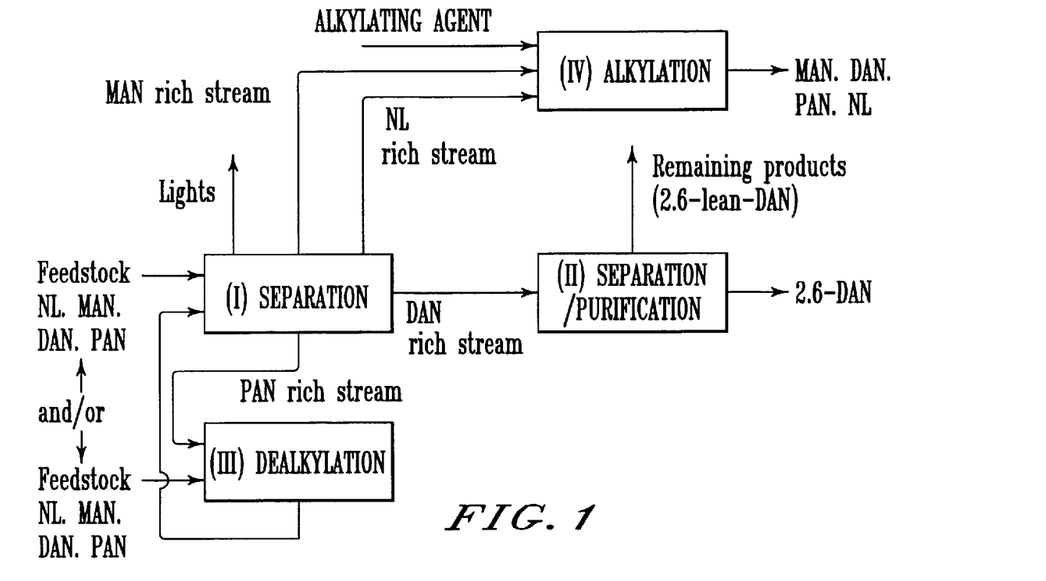
FIG. 1 shows the preferred scheme of a process in accordance with claim 1.

The separation and purification of step II purifies the 2,6-DAN and separates the 2,6-lean-DAN from the DAN fraction of step I, as can be seen from FIG. 1.

Separation and purification of 2,6-dialkylnaphthalene of step II may be conducted by conventional methods known to those of ordinary skill in the art such as cooling crystallization and/or adsorption. For example, separation and purification may be affected by using a method of crystallization under high pressure. In general, a liquid mixture containing two or more substances is pressurized, and a certain substance in the mixture is solidified and separated from the residual liquid by the effect of the pressure. In other words, this method involves a separating and purifying technique wherein a liquid mixture containing two or more substances is placed in a tightly sealed pressure vessel, a portion of the desired substance, 2,6-dialkylnaphthalene, is solidified to form a solid-liquid co-existing state, the liquid is discharged from the co-existing system while maintaining the pressure of the solid-liquid co-existing system at a higher level than equilibrium pressure of the objective substance, then the solid remaining in the vessel is pressed for discharging the residual liquid between the solid particles and integrating the solid particles. This technique is generally described in U.S. Pat. No. 5,220,098, the entire contents of which are hereby incorporated by reference.

The method involves injecting the slurry or liquid of the temperature of 70 to 120° C., preferably 80 to 100° C., into a high pressure vessel for conducting a crystallization under high pressure, adiabatically pressurizing the vessel to a pressure of from 300 to 4,000 kgf/cm$^2$, preferably 500 to 2,000 kgf/cm$^2$ to increase the quantity, i.e. the amount of 2,6-dialkylnaphthalene crystals, whereby coexistence of solid-liquid phases exist at the high pressure conditions; discharging the liquid phase component from the high pressure vessel, the discharging being conducted under pressure, to increase the ratio of the solid phase relative to the liquid phase within the vessel; lowering the pressure of the residual liquid phase so as to dissolve partially and purify the product; discharging the residual liquid phase by applying pressure to the solid phase within the high pressure vessel whereby a 2,6-dialkylnaphthalene crystal block having a high purity is obtained within the high pressure vessel. By this technique, a purity of 2,6 dialkylnaphthalene (e.g. 2,6-dimethylnaphthylene) of 98% by weight, preferably 99% by weight may be obtained.

In the separation and purification of step II, prior to the cooling crystallization and/or crystallization under high pressure, 2,6-dialkylnaphthalene can be pre-concentrated from dialkylnaphthalene mixture by fixed bed adsorptive separation system. As for the preconcentration of 2,6-DMN, it is preferable that the adsorption includes an adsorbent of a zeolite Y containing alkali metal and a desorbent of an organic solvent mainly composed of at least one component selected from the group consisting of hexane, octane, alkylbenzene, and cyclohexane. As alkylbenzene, mesitylene, o-xylene, and n-xylene are preferable.

At the cooling crystallization in the separation and purification step, since 2,6-DMN and 2,7-DMN form an eutectic crystal at the weight ratio of 0.7 (=2,6-DMN/2,7-DMN), only the low yield of 2,6-DMN is achieved. The theoretical 2,6-DMN separation yield is given by the following equations:

Yield (%)=(1−0.7/k)×100, where k=2,6-DMN/2,7-DMN at the feed of cooling crystallizer.

Therefore, it is most especially preferable to increase the ratio of 2,6-DMN/2,7-DMN for the higher yield of 2,6-DMN. The fixed bed adsorption can increase the ratio from 1.0 at the feed to 2.0 and more at output, which results in higher separation yields and much lower internal recycling amounts of the overall process.

Figure 5:
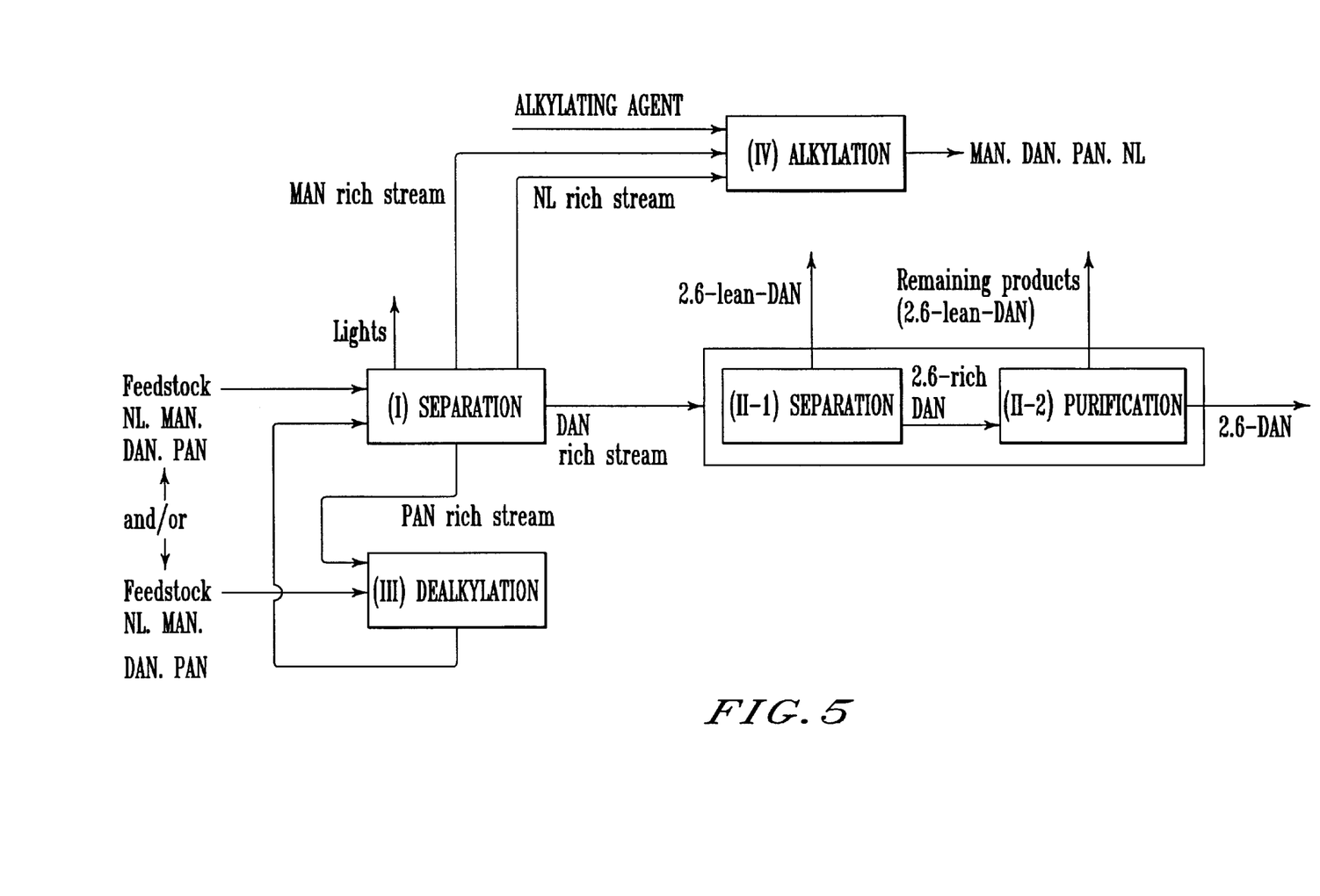
FIG. 5 shows the preferred scheme of a process in accordance with claim 5.

Preferably, for more effective production, the separation and purification of step II can be separated into separation section step II-1 and purification section step II-2, as can be seen from FIG. 5. In step II-1, the DAN fraction of step I is separated into 2,6-rich-DAN and 2,6-lean-DAN, and in step II-2, 2,6-DAN is purified from the 2,6-rich-DAN fraction from step II-1.

For example, separation of step II-1 may be preferably conducted by using distillation, and purification of step II-2 may be conducted by using cooling crystallization and/or crystallization under high pressure. By such a system, the 2,6-lean-DAN which contains little 2,7-DAN is separated by step II-1, and the 2,6-lean-DAN which contains much 2,7-DAN is separated by step II-2 as a remaining product of purification.

The conditions of HDA of step III include a temperature of about 200 to 1,000° C., and preferably 300 to 700° C., and a pressure of 0 to 250 atmospheres and preferably 5 to 150 atmospheres, a hydrogen circulation rate of from about 500 to 3,000 scf/bbl. The reaction is suitably accomplished utilizing a feed space velocity of about 0.1 to 10.0 hr$^{-1}$.

One example of a suitable catalyst for HDA, is an activated alumina supported catalyst bearing an oxide of Group VIII metal, preferably, chromium.

One more example of a suitable catalyst for HDA, is an activated alumina supported catalyst bearing an oxide of Group VIII metal and a Group VI metal, preferably, cobalt and molybdenum. The said oxide may be preferably pretreated at a temperature of 600 to 1000° F. in the presence of organic sulfide.

Other preferred catalysts for HDA include catalysts including a metal selected from the group consisting of noble metal, nickel, and combinations thereof, and a synthetic zeolite characterized by an X-ray diffraction pattern including interplanar d-spacing and relative intensity I/I$_o$× 100 as follows:

| 12.36 ± 0.4 | M-VS |
|---|---|
| 11.03 ± 0.2 | M-S |

| | |
|---|---|
| 8.83 ± 0.14 | M-VS |
| 6.18 ± 0.12 | M-VS |
| 6.00 ± 0.10 | W-M |

4.06±0.07 W-S
3.91±0.07 M-VS
3.42±0.06 VS.

The preferable noble metal is selected from the group consisting of platinum, palladium, and combinations thereof.

The conditions of alkylation of step IV preferably include a temperature of about 0 to 500° C., and preferably 240 and 450° C., and a pressure of between 0 to 250 atmospheres and preferably 1 to 50 atmospheres. The mole ratio of alkylating agent to feed of monoalkylnaphthalene or naphthalene can be from about 20:1 to 1:20, preferably from 10:1 to 1:10. The reaction is suitably accomplished utilizing a feed space velocity of about 0.1 to 10.0 $hr^{-1}$.

Preferred alkylating agents include alcohols, olefins, aldehydes, halides, and ethers. For example, methanol, dimethylether and polyalkylbenzene are preferred. Methanol and dimethylether are especially preferred.

A suitable catalyst for alkylation is a synthetic zeolite characterized by an X-ray diffraction pattern including interplanar d-spacing and relative intensity $I/I_o \times 100$ as follows:

| | |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

A suitable catalyst is described in U.S. Pat. No. 5,001,295, as MCM-22, the entire contents of which are hereby incorporated by reference.

Preferably, the alkylation can be carried out in any of the known reactors usually employed for alkylation. For example, a tubular reactor with a downflow of reactants over a fixed bed of catalyst can be employed.

In order to maintain high feedstock conversion, the injection of methanol to reactor can be performed, preferably, in multiple stages, and more preferably two stages. For example, one reactor with top and middle methanol feed, or two reactors in series with top and intermediate methanol feed are preferably used.

Figure 6:
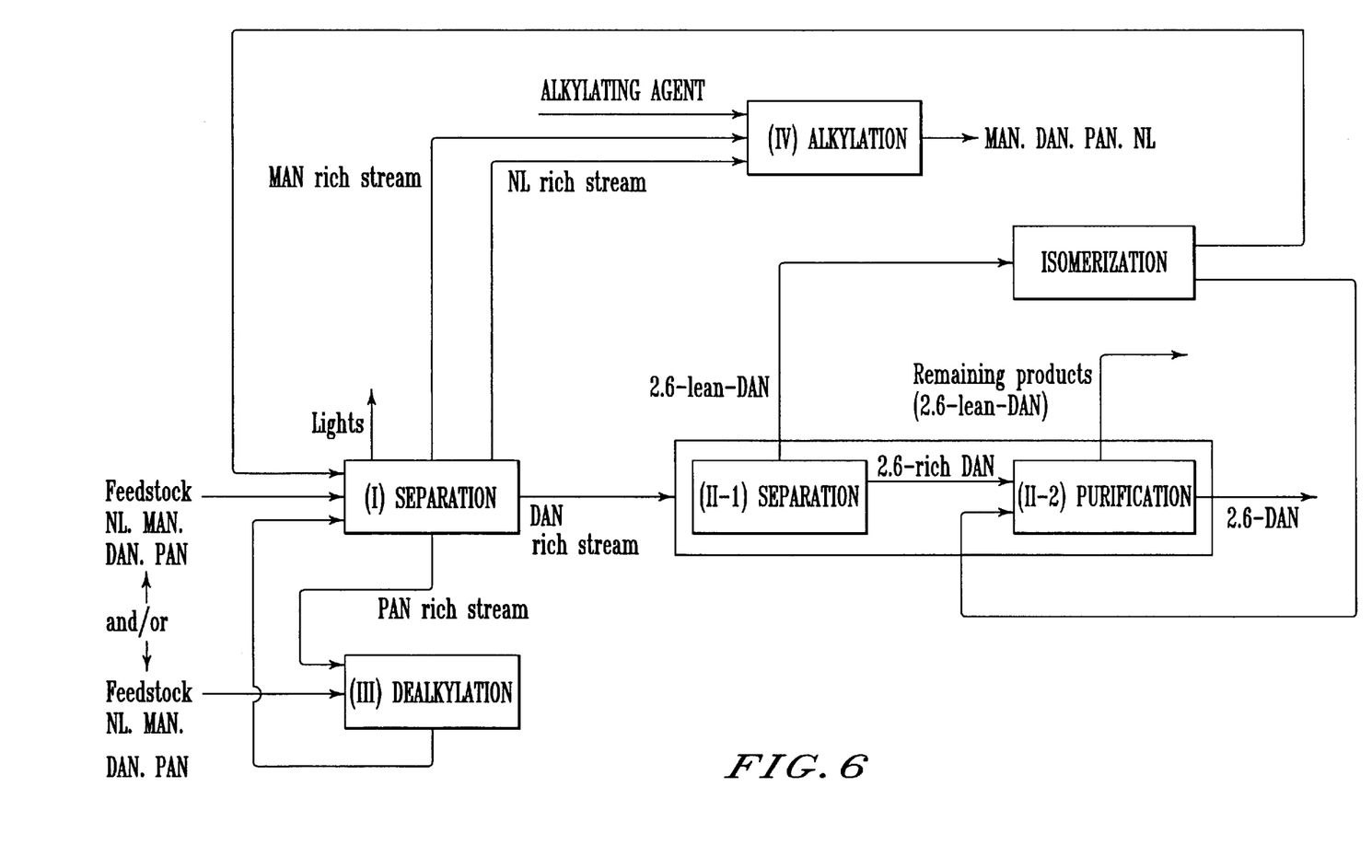
FIG. 6 shows the preferred scheme of a process in accordance with claim 6.
Figure 7:
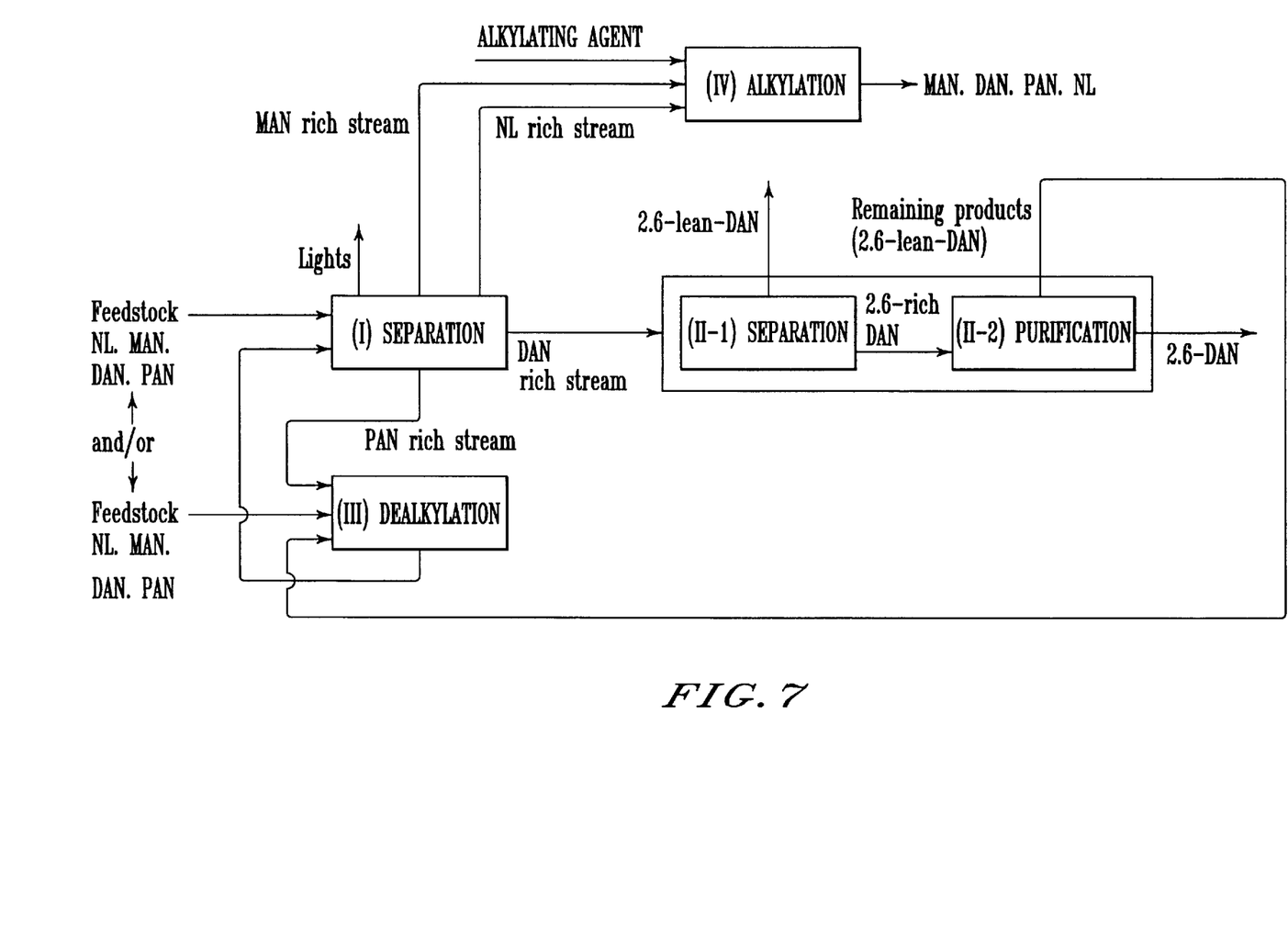
FIG. 7 shows the preferred scheme of a process in accordance with claim 8.

In a preferred embodiment, the 2,6-lean-DAN fraction from step II-1 may be subjected to isomerization conditions to provide for a dialkylnaphthalene fraction which has a greater content of 2,6-dialkylnaphthalene, as can be seen from FIG. 6. Preferably, the product of the isomerization may be fed to step I and/or step II-2 for more efficient recovery.

Preferred isomerization conditions are generally disclosed in co-pending application U.S. application Ser. No. 08/661,114 (the entire contents of which are hereby incorporated by reference), and are suitable for conducting simultaneous transalkylation of dialkylnaphthalene and naphthalene, and isomerization of dialkylnaphthalenes.

A preferred catalyst for isomerization is a synthetic zeolite characterized by an X-ray diffraction pattern including interplanar d-spacing and relative intensity $I/I_o \times 100$ as follows:

| | |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS. |

A suitable catalyst is described in U.S. Pat. No. 5,001,295, as MCM-22, the entire contents of which are hereby incorporated by reference.

Preferably, isomerization is conducted at a weight hourly space velocity (WHSV) of dialkylnaphthalenes of 0.1 to 10, preferably 0.5 to 5 $h^{-1}$, more preferably 0.75 to 1.5 $h^{-1}$.

Preferably, isomerization is conducted at a temperature of from 100 to 500° C., preferably 150 to 350° C., more preferably 200 to 300° C.

Preferably, isomerization is conducted at a pressure of atmospheric to 100 $kgf/cm^2$, preferably atmospheric to 30 $kcf/cm^2$.

During isomerization it is optionally preferable to co-feed hydrogen in an amount of 0.1 to 10 $mol-H_2/mol$-hydrocarbons.

Figure 2:
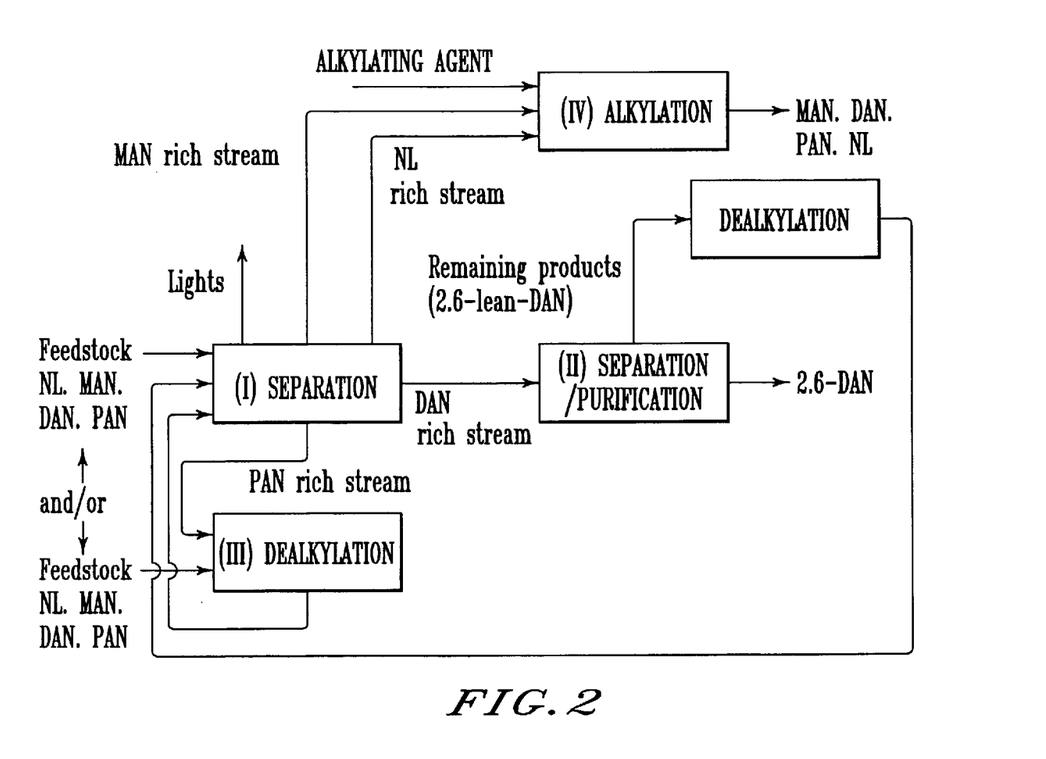
FIG. 2 shows the preferred scheme of a process in accordance with claim 2.
Figure 3:
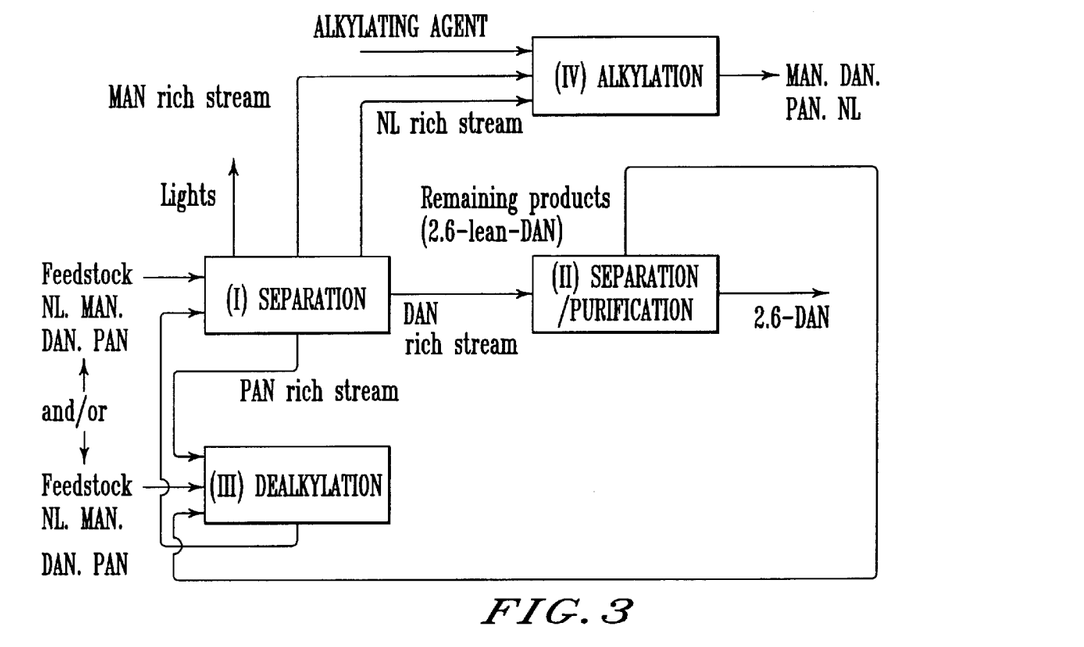
FIG. 3 shows the preferred scheme of a process in accordance with claim 3.

According to the preferred embodiment of FIGS. 2 or 3, 2,6-dialkylnaphthalene may be prepared from hydrocarbon feedstocks as follows:

I. separating a feedstock and/or a product fed from step III into a fraction containing naphthalene, a fraction containing monoalkynaphthalene, a fraction containing dialkylnaphthalene and a fraction containing remaining products, II. separating and purifying 2,6-dialkylnaphthalene from the dialkylnaphthalene fraction of step I, IIIa. dealkylating a dialkylnaphthalene fraction after 2,6-dialkylnaphthalene is separated therefrom in step II and recycling a product of dealkylation to step I;

IIIb. dealkylating the feedstock and/or the fraction containing remaining products of step I and feeding the product of dealkylation to step I;

V. alkylating the fractions containing naphthalene and monoalkynaphthalene of step I.

In this process, 2,6-lean-DAN as remaining product of separation/purification of step II is dealkylated and fed to separation of step I. So, 2,6-DAN isomers in 2,6-lean-DAN may be changed to MMN or NL and can be alkylated in step IV.

Figure 4:
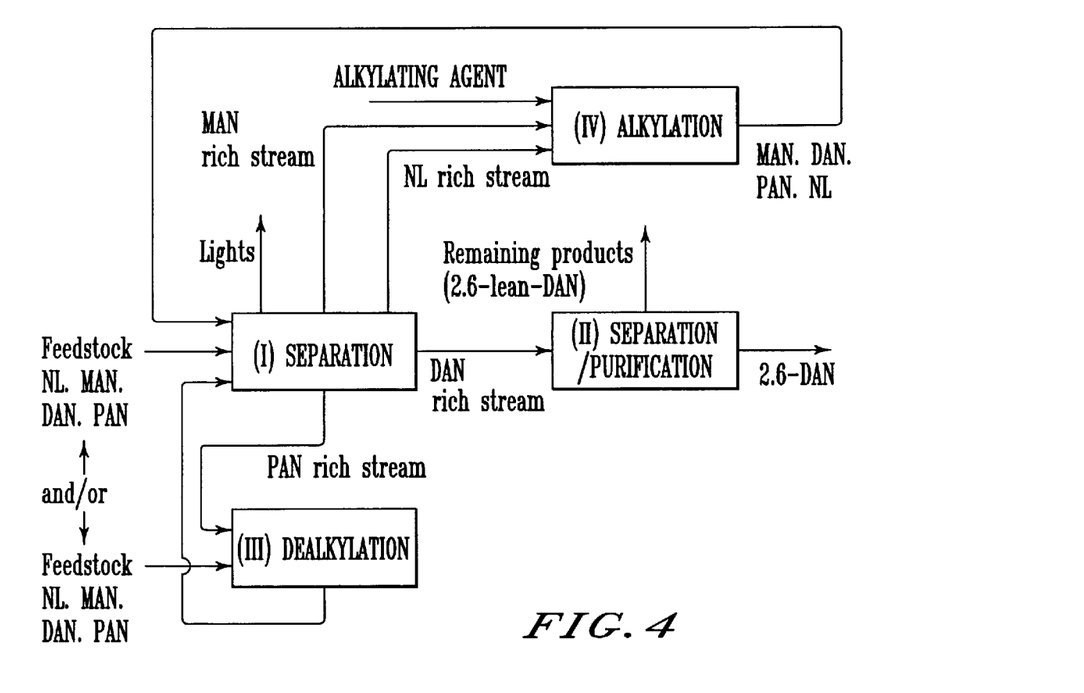
FIG. 4 shows the preferred scheme of a process in accordance with claim 4.

As for the preferred embodiment in FIG. 4, the product of alkylation of step IV is fed to separation of step I. Accordingly, PAN produced in step IV can be separated in step I and fed to dealkylated in step III. Therefore, it enables to provide the effective utilization of PAN and allows much higher feedstock conversion at alkylation step, as already described.

Figure 8:
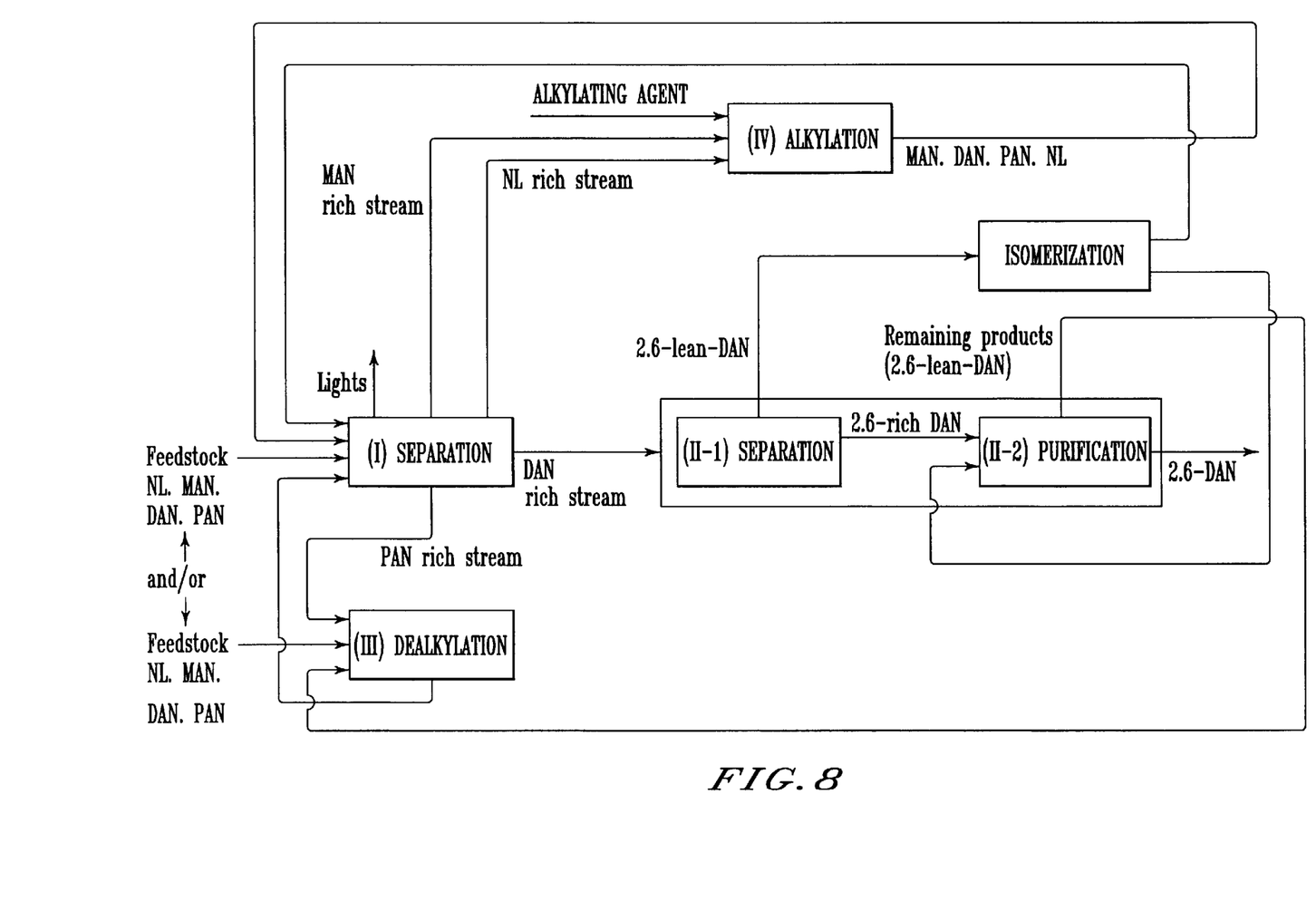
FIG. 8 shows the preferred scheme of a process in accordance with claim 9.

The process scheme of FIG. 8 is a most preferable embodiment of the present invention.

EXAMPLES

Having generally described this invention, a further understanding can be obtained by reference to certain specific examples, which are provided herein for purposes of illustration only and are not intended to be limiting unless otherwise specified.

Example 1

Alkylation of MMN and Naphthalene

A 153 g amount of MCM-22 catalyst is charged into a tubular reactor (volume:370 cc). As a feedstock for alkylation, 1-MMN, 2-MMN and naphthalene are used, and mixed at a molar ratio of 2.2 of 2-MMN/1-MMN, and a weight ratio of 3.0 of MMN's (1-MMN+2-MMN)/naphthalene.

Thereupon, the feedstock is supplied to the reactor (254 C, 5 kg/cm$^2$) at a rate of 153.4 g/hr and 1.0 hr$^{-1}$ in WHSV with a feed of hydrogen at the rate of 1.8 ft$^3$/hr. Four hours later, methanol, as an alkylating agent, is introduced into the reactor at 35.5 g/hr, and alkylation is conducted for 20 hours. The product obtained is analyzed by gas chromatography, and the results are summarized in Table 1.

TABLE 1

(Alkylation of Monomethylnaphthalene and Naphthalene)

|  | Before Reaction | After Reaction |
|---|---|---|
| Component (wt %) |  |  |
| dimethylnaphthalene | 0 | 17.19 |
| 2,6-DMN | 0 | 1.72 |
| 2,7-DMN | 0 | 1.20 |
| other isomers | 0 | 14.27 |
| monomethylnaphthalene | 73.63 | 60.10 |
| 2-MMN | 50.55 | 40.32 |
| 1-MMN | 23.08 | 19.78 |
| naphthalene | 25.28 | 18.67 |
| other component | 1.00 | 3.91 |
| Evaluation |  |  |
| NL conversion (%) | — | 26.15 |
| 2-MMN/1-MMN | 2.2 | 2.04 |
| MMN conversion (%) | — | 18.37 |
| 2,6-DMN/total DMN (%) | — | 10.02 |
| 2,6-DMN/2,7-DMN | — | 1.44 |

As can be seen from Table 1, the ratio of 2,6-DMN/2,7-DMN is over 1.1 and the ratio of 2-MMN/1-MMN is over 2.0.

Example 2

(Alkylation)

153 g of MCM-22 were charged in the tubular reactor (volume: 370 cc). As a feedstock for alkylation, 1-MMN (purity 95.5%) and 2-MMN (purity 96.6%) were used, and mixed at the molar ratio of 2.2 of 2-MMN/1-MMN. Feedstock was supplied in the reactor (350° C.) at the rate of 76.7 g/hr and 0.5 hr$^{-1}$ in WHSV for 4 hours. Thereafter, methanol was started to be supplied in the reactor at the rate of 17.3 g/hr and the reaction was proceeded for 20 hours. The obtained product was analyzed by gas chromatography, and the result is summarized in Table 2.

TABLE 2

(Alkylation)

|  | before reaction | after reaction |
|---|---|---|
| component (wt %) |  |  |
| dimethylnaphthalene | 0 | 35.45 |
| 2,6-DMN | 0 | 5.12 |
| 2,7-DMN | 0 | 4.44 |
| other isomers | 0 | 25.89 |
| monomethylnaphthalene | 98.66 | 41.16 |
| 2-MMN | 67.61 | 28.84 |
| 1-MMN | 31.05 | 12.32 |

TABLE 2-continued (Alkylation)

|  | before reaction | after reaction |
|---|---|---|
| naphthalene | 0 | 0.19 |
| other component (mainly PAN) | 1.53 | 23.20 |
| evaluation |  |  |
| 2-MMN/1-MMN | 2.2 | 2.3 |
| MMN conversion (%) | — | 58.28 |
| 2,6-DMN/total DMN (%) | — | 14.45 |
| 2,6-DMN/2,7-DMN | — | 1.16 |

As can be seen from Table 2, the ratio of 2,6-DMN/2,7-DMN is over 1.1 and the ratio of 2-MMN/1-MMN is over 2.0.

Example 3

(Alkylation and Distillation)

Alkylation of MMN and naphthalene has been carried out for several months in the same manner described in Example 1 and about 400 kg of the product is collected. Distillation of the product is carried out by using a batch type distillation tower with a packed column. A number of theoretical trays of the tower is expected to be at least 50. The operation pressure at the top of the column is controlled between 15 and 36 Torr and distillation proceeds at a reflux ratio of 50 to 75.

The product is separated into 17 fractions by differences in boiling points as shown in Table 3.

TABLE 3

(Alkylation and Distillation)

|  | Amount (kg) | DMN concentration (%) | 2,6-DMN concentration (%) |
|---|---|---|---|
| Fraction-1~10 | 270.8 | 0.0 | not analyzed |
| Fraction-11 | 30.9 | 0.5 | not analyzed |
| Fraction-12 | 8.8 | 38.9 | not analyzed |
| Fraction-13 | 11.0 | 64.8 | 11.2 |
| Fraction-14 | 6.3 | 92.3 | 25.4 |
| Fraction-15 | 15.7 | 99.6 | 4.3 |
| Fraction-16 | 4.8 | 98.7 | 0.0 |
| Fraction-17 | 5.3 | 41.6 | 0.0 |
| Residue | 21.2 | 0.0 | 0.0 |

Example 4

(Hydrodealkylation)

A part of Fraction-17 and Residue shown in Table 3 are mixed to prepare the feedstock(Blend-A) for hydrodealkylation. A 50 g amount of $Cr_2O_3/Al_2O_3$ type catalyst produced by Sud-Chemie AG is charged into a tubular reactor. The reactor is heated gradually from ambient temperature to 662° F. to dry the catalyst while supplying hydrogen gas. Thereupon Blend-A is fed to the reactor at the rate of 50 g/hr and 1.0 hr$^{-1}$ in WHSV, while supplying hydrogen gas at 1.2 scf/hr. Hydrodealkylation is carried out at 887° F. and 854 psig. The product is analyzed by GC and the results of hydrodealkylation are summarized in Table 4 below.

As shown in Table 4, $Cr_2O_3/Al_2O_3$ type catalyst is effective to enrich 2,6-DMN from 2,6-DMN lean feed.

TABLE 4

(Hydrodealkylation)

| | Feed (Blend-A) | HDA Product |
|---|---|---|
| naphthalene | 0.0 | 3.11 |
| 2-MN | 0.0 | 15.68 |
| 1-MN | 0.0 | 3.71 |
| 2-EN | 0.0 | 0.57 |
| 1-EN | 0.0 | 0.26 |
| 2,6-DMN | 0.0 | 4.86 |
| 2,7-DMN | 0.0 | 4.58 |
| 1,3- + 1,7-DMN | 0.0 | 7.58 |
| 1,6-DMN | 0.0 | 2.92 |
| 2,3- + 1,4-DMN | 0.14 | 4.84 |
| 1,5-DMN | 0.0 | 0.39 |
| 1,2-DMN | 20.18 | 9.42 |
| 1,8-DMN | 0.0 | 0.12 |
| Unknowns before first DMN | 0.0 | 2.50 |
| Unknowns between DMN | 1.34 | 0.39 |
| Heavies Including Polymethylnaphthalenes | 78.34 | 39.08 |
| Total DMNs (%) | 20.28 | 34.71 |
| 2,6-DMN/Total DMNs (%) | 0.0 | 13.20 |

Example 5

Isomerization

A 25 g amount of MCM-22 catalyst is charged into the tubular reactor (volume: 200 cc). The reactor is heated gradually from ambient temperature to 400° C. to dry the catalyst while supplying nitrogen gas, and the flow of nitrogen gas is ceased when the temperature becomes stable at 400° C. Thereupon, 2,6-lean-DMN is supplied to the reactor at the rate of 25 g/hr and 1.0 $hr^{-1}$ in WHSV, and isomerization of DMN is carried out for four hours. The contents of the obtained product are analyzed by gas chromatography, and the results are summarized in Table 5.

TABLE 5

(Isomerization)

| | before reaction | After reaction |
|---|---|---|
| Component (wt %) | | |
| dimethylnaphthalene | 98.09 | 80.10 |
| 2,6-DMN | 6.21 | 13.96 |
| 2,7-DMN | 8.48 | 8.66 |
| other isomers | 83.40 | 57.48 |
| monoethylnaphthalene | 0.20 | 9.77 |
| 2-MMN | 0.03 | 6.71 |
| 1-MMN | 0.17 | 3.06 |
| naphthalene | 0 | 0.78 |
| other component | 1.71 | 9.35 |
| evaluation | | |
| 2,6-DMN/total DMN (%) | 6.3 | 17.4 |
| 2,6-DMN/2,7-DMN | 0.73 | 1.61 |

Example 6

Separation and Purification (1) Crystallization under High Pressure Crystallization A 1,505 g amount of DMN isomers is supplied into the high pressure crystallizer (KOBELCO 1.5 L type), and 236 g of 2,6-DNN crystals (purity 87%) are separated under the condition of 2,000 kgf/cm$^2$ and 45° C.

(2) Cooling Crystallization

Using a vessel for crystallization (3 liter), 2,001 g of DMN isomers is cooled quickly from 50 to 40° C. with slow stirring. Then, 0.5 g of seed crystals are charged to the vessel which is kept at a temperature at 40° C. for an hour. Thereupon, the feedstock is cooled to 10° C. at 2° C./min. A 360 g amount of 2,6-DMN crystals (purity 68%) is separated by filtration under pressure.

The results of separation by both crystallization under high pressure and cooling crystallization are summarized in Table 6.

TABLE 6

(Separation and Purification)

| Component (g) | before crystallization | crystal | filtrate |
|---|---|---|---|
| CRYSTALLIZATION UNDER HIGH PRESSURE | | | |
| 2,6-DMN | 301 | 205 | 96 |
| 2,7-DMN | 232 | 22 | 210 |
| other DMN | 972 | 9 | 963 |
| TOTAL | 1505 | 236 | 1269 |
| 2,6-DMN/2,7-DMN | 1.3 | — | 0.5 |
| 2,6-DMN/total DMN | 20.0% | — | 7.6% |
| purity of crystal | — | 87% | — |
| recovery of 2,6-DMN | — | 68% | — |
| yield of 2,6-DMN | — | 13.6% | — |
| COOLING CRYSTALLIZATION | | | |
| 2,6-DMN | 400 | 244 | 156 |
| 2,7-DMN | 308 | 67 | 241 |
| other DMN | 1293 | 49 | 1244 |
| TOTAL | 2001 | 360 | 1641 |
| 2,6-DMN/2,7-DMN | 1.3 | — | 0.65 |
| 2,6-DMN/total DMN | 20.0% | — | 9.5% |
| purity of crystal | — | 68% | — |
| recovery of 2,6-DMN | — | 61% | — |
| yield of 2,6-DMN | — | 12.2% | — |

"Recovery of 2,6-DMN" means the content of 2,6-DMN in the crystals against the content of 2,6-DMN in the feedstock.

"Yield of 2,6-DMN" means the content of 2,6-DMN in the crystal against the total weight of feedstock.

As shown in Table 6, the yield of 2,6-DMN by crystallization under high pressure is much higher than by cooling crystallization. Further, the 2,6-DMN/total-DMN ratio of the filtrate by crystallization under high pressure is less than 8%. Therefore, the filtrate is more effective as a feedstock for transalkylation and isomerization of 2,6-lean-DMN.

Furthermore, when an attempt is made to increase the purity of crystals by cooling crystallization, the yield of 2,6-DMN decreases drastically.

Example 7

(Purification)

Pre-condensation of 2,6-DMN from DMN mixture (Table 7) was tried by cooling crystallization and a 2,6-DMN rich cake, which is to be used as feedstock for the crystallization under high pressure, was separated by bench scale pressure filtration unit.

Purification of 2,6-DMN from the 2,6-DMN rich cake was carried out by the crystallization under high pressure method using Kobelco's HPC test machine.

Figure 9:
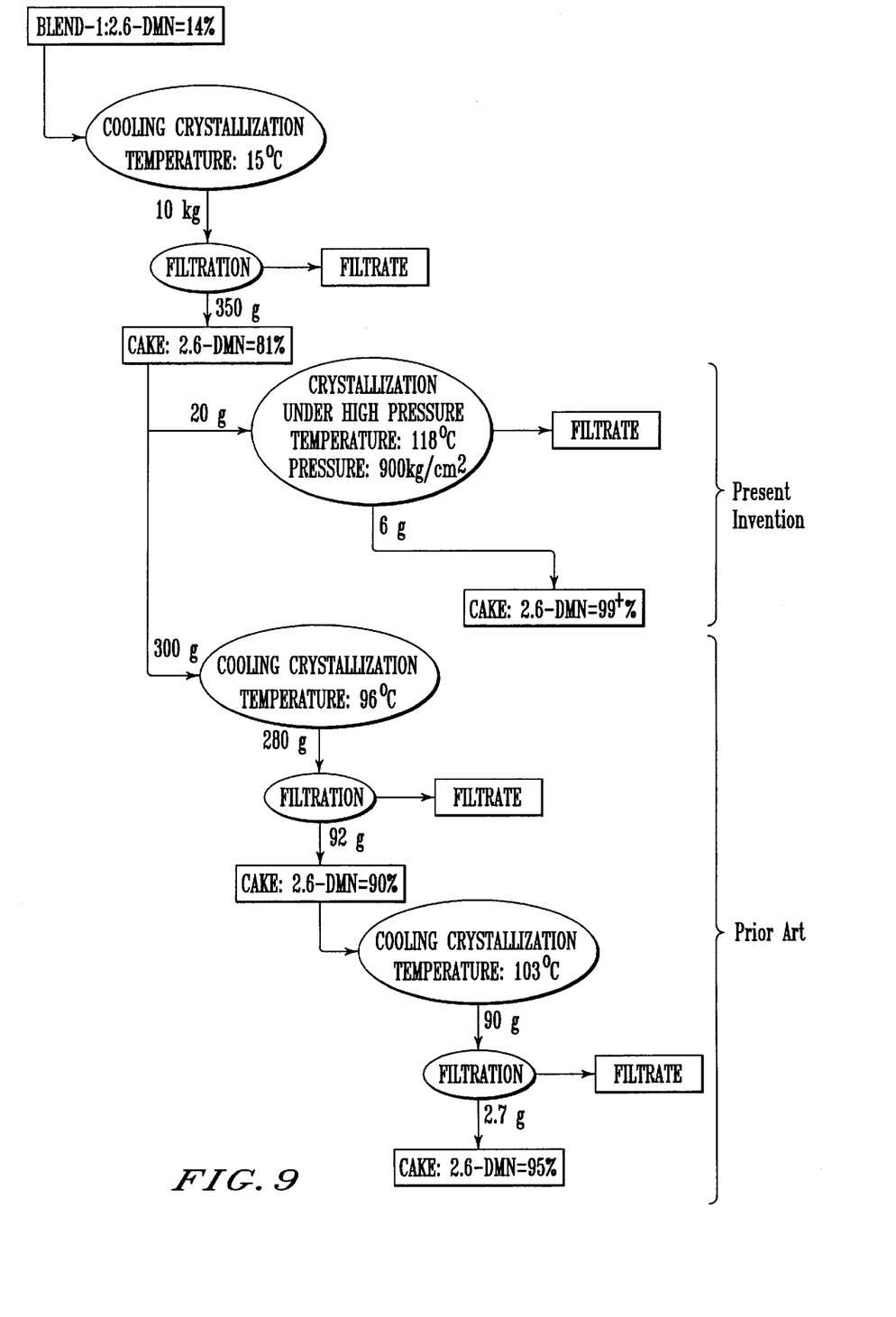
FIG. 9 shows the results of Example 7.

Several series of experiments were performed and results are summarized in FIG. 9.

As can be seen in FIG. 9, crystallization under high pressure achieves more effective purification performance in separation yield and 2,6-DMN purity by single stage crystallization than does two-stage Cooling Crystallization.

TABLE 7

(Composition of DMN Mixture)

|  | DMN mixture |
|---|---|
| Sulfur (ppm) | 43.0 |
| Nitrogen (ppm) | 140 |
| 2,6-DMN | 13.8 |
| 2,7-DMN | 14.1 |
| 1,6-DMN | 7.1 |
| 1,3- & 1,7-DMN | 20.5 |
| 1,4-DMN | — |
| 1,2- & 1,5-DMN | 0.4 |
| 2,3-DMN | 0.5 |
| Others | 43.6 |

Example 8

(Distillation)

Two types of batch distillation tower are used for the separation of alkylnaphthalenes from LCO. One of the distillation tower (Fractioneer-A) has 167 liters still and 32 foot long column with PRO-PAK (Scientific Development Company) and the other distillation tower (Fractioneer-B) has 27 liters still with an 11 foot long column with PRO-PAK. 164 kg of LCO is charged into the Fractioneer-A and distillation is carried out at a reflux ratio of 50 and a pressure of 60 Torr. 80.5 liters are taken at a take off rate of 0.7 liters per hour.

Then 25 kg of the residue in the still of Fractioneer-A is taken out after the first distillation and charged into Fractioneer-B. Another batch distillation is carried out at a reflux ratio of 50 and a pressure of 50 Torr. 14 liters are taken at a take off rate of 125 ml per hour. The components of the product (Blend-B) obtained from the above-mentioned two step distillation are shown in Table 8.

Example 9

(Hydrodealkylation)

A 70 g amount of $Cr_2O_3/Al_2O_3$ type catalyst produced by Sud-Chemie AG is charged into a tubular reactor. The reactor is heated gradually from ambient temperature to 932° F. to dry the catalyst while supplying hydrogen gas. Thereupon distillation product (Blend-B) obtained from Example 8 is supplied to the reactor at the rate of 70 g/hr and 1.0 $hr^{-1}$ in WHSV, while supplying hydrogen gas at 0.98 scf/hr. The hydrodealkylation reaction is carried out at 933° F. and 1138 psig. The product is analyzed by GC and the results of hydrodealkylation are summarized in Table 8 below.

Example 10

(Hydrodealkylation)

A 70 g amount of $CoO/MoO_3/Al_2O_3$ type catalyst produced by Akzo Chemicals Inc. is charged into a tubular reactor. The reactor is heated gradually from ambient temperature to 300° F. with nitrogen flow at 5 scf/hr. Then the flow gas is switched to hydrogen at 2 scf/hr and pressure is increased to 500 psig. Catalyst is contacted with an organic sulfide (Kerosene with 1.0% of Dimethyldisulfide) for sulfiding while supplying hydrogen gas and then temperature is raised to 650° F. Thereupon distillation product (Blend-B) obtained from Example 8 is fed to the reactor at the rate of 70 g/hr and 1.0 $hr^{-1}$ in WHSV, while supplying hydrogen gas at 0.98 scf/hr. Hydrodealkylation is carried out at 932° F. and 1425 psig The product is analyzed by GC and the results of hydrodealkylation are summarized in Table 8 below.

As shown in Table 8, both $Cr_2O_3/Al_2O_3$, and $CoO/MoO_3/Al_2O_3$ type catalyst are effective to enrich DMN isomers from DMN lean feed.

TABLE 8

(Hydrodealkylation)

|  | Example 7 Distillation Product (Blend-B) | Example 8 HDA Product | Example 9 HDA Product |
|---|---|---|---|
| Catalyst |  | $Cr_2O_3/Al_2O_3$ | $CoO/MoO_3/Al_2O_3$ |
| naphthalene | 0.0 | 1.33 | 4.75 |
| 2-MN | 0.0 | 4.31 | 9.48 |
| 1-MN | 0.0 | 1.05 | 2.44 |
| 2-EN | 0.0 | 1.56 | 2.13 |
| 1-EN | 0.0 | 0.36 | 0.44 |
| 2,6-DMN | 0.0 | 2.46 | 3.53 |
| 2,7-DMN | 0.0 | 2.56 | 3.76 |
| 1,3- + 1,7-DMN | 0.0 | 2.55 | 3.82 |
| 1,6-DMN | 0.0 | 1.43 | 2.17 |
| 2,3- + 1,4-DMN | 0.0 | 1.18 | 1.44 |
| 1,5-DMN | 0.0 | 0.24 | 0.34 |
| 1,2-DMN | 0.04 | 0.40 | 0.32 |
| 1,8-DMN | 0.04 | 0.25 | 0.47 |
| Unknowns before first DMN | 0.0 | 8.67 | 17.68 |
| Unknowns between DMN | 0.0 | 0.54 | 0.68 |
| Heavies including polymethylnaphthalenes | 99.92 | 71.11 | 46.56 |
| Total DMNs (%) | 0.08 | 11.07 | 15.85 |
| 2,6-DMN-Total DMNs | 0.0 | 22.22 | 22.27 |

Example 11

(Distillation and Hydrotreating)

164 kg of LCO is charged into the Fractioneer-A and distillation is carried out at a reflux ratio of 50 and a pressure of 60 Torr. 120 liters are taken at a take off rate of 0.7 liters per hour and prepared for hydrotreating feedstock as Blend-C. NiO/MoO$_3$/Al$_2$O$_3$ type catalyst produced by Akzo Chemicals Inc. is chosen as a hydrotreating catalyst and charged into a tubular reactor.

After drying and sulfiding catalyst, then Blend-C is fed into the reactor at the rate of 0.43 hr$^{-1}$ in WHSV and hydrotreating is carried out at 400 psig and 726° F., while supplying hydrogen gas at 3495 scf/bbl. The results of hydrotreating are summarized in Table 9 below.

As shown in Table 9, NiO/MoO$_3$/Al$_2$O$_3$ type catalyst is effective to reduce the nitrogen and/or sulfur compounds in LCO with minimum loss of DMN isomers.

TABLE 9

(Distillation and Hydrotreating)

| | Nit. ppm | Sul. ppm | API | 400F+ Conv. (%) | 400F+ Conv. (%) | 500F+ Conv. (%) | Total DMNs wt % |
|---|---|---|---|---|---|---|---|
| Blend-C | 230 | 388 | 18.7 | — | — | — | 26.56 |
| HDT Product | 7 | 5 | 20.6 | 0.6 | 7 | 21 | 21.24 |

Example 12

(Adsorption)

2,6-DMN and 2,7-DMN are mixed and dissolved into iso-octane at 2.0 wt % of concentration respectively. Then DMN-isooctane solution is fed to the adsorption column (4.6 mm ID and 500 mmL) packed with K-Y zeolite at the rate of 0.50 ml/min, while column temperature is controlled at 158° F. Time course data of the DMN concentration in the effluent is gathered by GC analysis and breakthrough curve in adsorption step is obtained.

After the adsorption step, liquid feed is switched to the pure iso-octane and effluent is also analyzed to gather the time course data of the DMN concentration in the effluent.

Figure 10A:
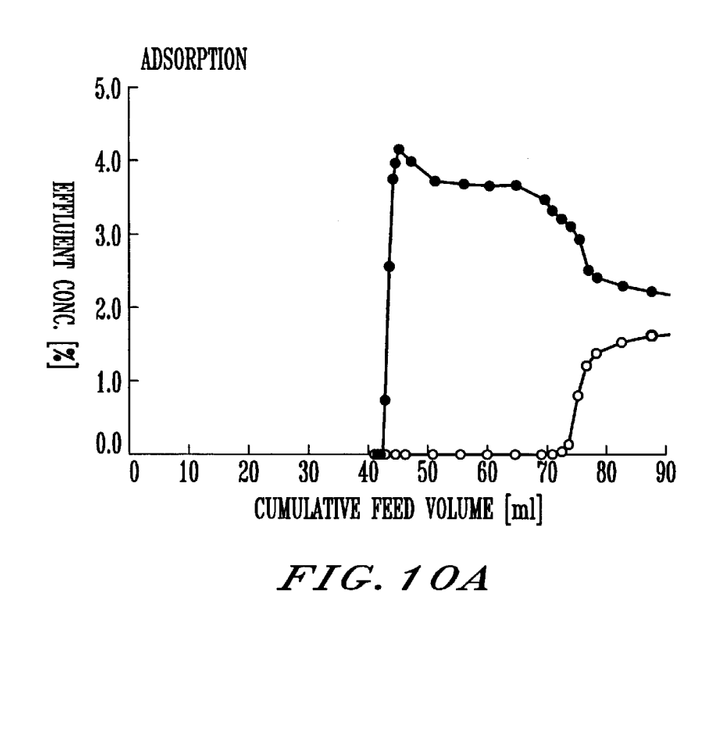
FIG. 10 shows the results of Example 12.
Figure 10B:
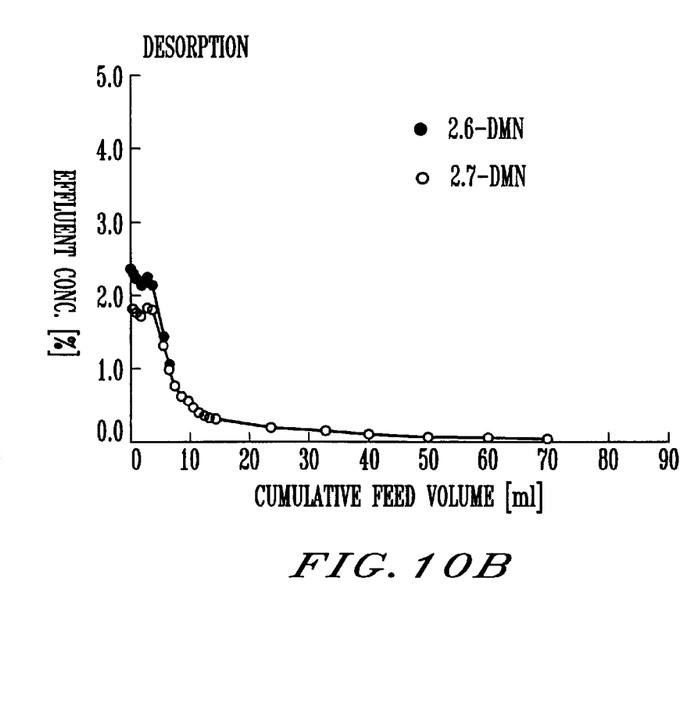

The results of the breakthrough curve and desorption curve are summarized in FIG. 10. As shown in the figure, 2,7-DMN is priorly adsorbed in zeolite compared to 2,6-DMN and it is obviously possible to improve 2,6-/2,7-DMN by contacting DMN isomers with the K-Y type zeolite.

Example 13

Figure 11A:
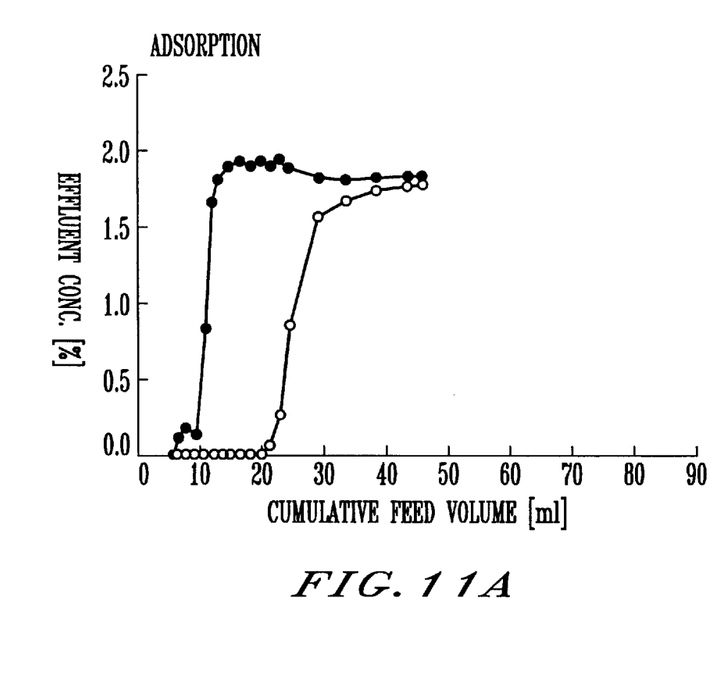
FIG. 11 shows the results of Example 13.
Figure 11B:
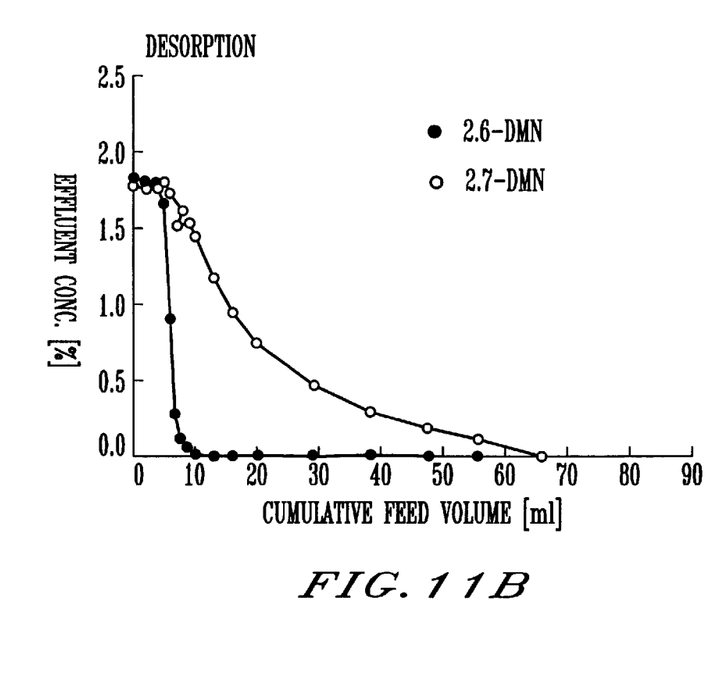

Another adsorption test is carried out in the same manner described in Example 12 except that mesitylene is used as a solvent. The results of the breakthrough curve and desorption curve are summarized in FIG. 11.

Obviously, numerous modifications and variations of the present invention are possible in light of the above teachings. It is therefore to be understood that within the scope of the appended claims, the invention may be practiced otherwise than as specifically described herein.

This application is based on U.S. application Ser. No. 08/948,299, filed Oct. 10, 1997, the entire contents of which are hereby incorporated by reference.

What is claimed as new and is desired to be secured by Letters Patent of the United States is:

1. A process for producing 2,6-dialkylnaphthalene from a hydrocarbon feedstock, comprising the following steps:

I. separating the hydrocarbon feedstock and/or a dealkylation product fed from step III into a fraction comprising naphthalene, a fraction comprising monoalkylnaphthalene, a fraction comprising dialkylnaphthalene and a fraction comprising remaining products;

II. separating and purifying 2,6-dialkylnaphthalene from the dialkylnaphthalene fraction of step I;

III. dealkylating the hydrocarbon feedstock and/or the remaining products fraction of step I and feeding the dealkylation product to step I;

IV. alkylating the naphthalene and monoalkylnaphthalene fractions of step I;

wherein the hydrocarbon feedstock is fed to step I and/or step III.

2. The process of claim 1, further comprising dealkylating the dialkylnaphthalene fraction after 2,6-dialkylnaphthalene is separated therefrom in step II and recycling the dealkylation product obtained therefrom to step I.

3. The process of claim 1, wherein dealkylating the dialkylnaphthalene fraction after 2,6-dialkylnaphthalene is separated therefrom in step II is conducted in step III together with dealkylating the hydrocarbon feed stock and/or the remaining products fraction of step I.

4. The process of claim 1, wherein the product of step IV is fed to step I.

5. The process of claim 1, wherein step II comprises the following sub-steps:

II-1. separating the dialkylnaphthalene fraction of step I into a 2,6-rich-dialkylnaphthalene fraction and a 2,6-lean-dialkylnaphthalene fraction;

II-2. purifying 2,6-dialkylnaphthalene from the 2,6-rich-dialkylnaphthalene fraction from step II-1.

6. The process of claim 5, further comprising isomerizing at least a part of the 2,6-lean-dialkylnaphthalene fraction from step II-1, wherein at least a part of the isomerization product is fed to step I and/or step II-2.

7. The process of claim 6, wherein the isomerizing is conducted in the presence of a catalyst composition comprising a synthetic zeolite characterized by an X-ray diffraction pattern including interplanar d-spacing (A)

12.36±0.4
11.03±0.2
8.83±0.14
6.18±0.12
6.00±0.10
4.06±0.07
3.91±0.07
3.42±0.06.

8. The process of claim 6, wherein at least a part of the product remaining after the 2,6-dialkylnaphthalene is purified in step II-2 is fed to step III.

9. The process of claim 6, wherein at least a part of the product from step IV is fed to step I, and wherein at least a part of the product remaining after the 2,6-dialkylnaphthalene is purified in step II-2 is fed to step III.

10. The process of claim 5, wherein the purifying comprises at least one means selected from the group consisting of crystallization under high pressure, cooling crystallization, and fixed bed adsorptive separation.

11. The process of claim 10, wherein the fixed bed adsorptive separation comprises contacting the 2,6-rich-dialkylnaphthalene fraction with an adsorbent of a zeolite Y containing alkali metal and a desorbent of an organic solvent comprising at least a component selected from the group consisting of hexane, octane, alkylbenzene, and cyclohexane.

12. The process of claim 1, wherein the hydrocarbon feedstock is product of pre-processing raw material, and wherein the pre-processing comprises at least one treatment selected from the group consisting of distillation, concentration, hydrotreating, de-sulfurization, de-nitrogenation and de-watering.

13. The process of claim 12, wherein the hydrotreating comprises contacting said raw material with a catalyst composition comprising an activated alumina catalyst support comprising an oxide of a Group VIII metal and a Group VI-A metal.

14. The process of claim 13, wherein the Group VIII metal is nickel.

15. The process of claim 13, wherein the Group VI-A metal is molybdenum.

16. The process of claim 13, wherein the oxide of metal is pre-treated at 600–1200° F. in the presence of a sulfur compound.

17. The process of claim 1, wherein the dealkylation in step I is hydrodealkylation.

18. The process of claim 17, wherein the hydrodealkylation comprises contacting said hydrocarbon feedstock with a catalyst composition comprising an activated alumina catalyst support comprising an oxide of a Group VI-A metal.

19. The process of claim 18, wherein the Group VI-A metal is chromium.

20. The process of claim 17, wherein the hydrodealkylation comprises contacting the hydrocarbon feedstock with a catalyst composition comprising an activated alumina catalyst support comprising an oxide of a Group VIII metal, and a Group VI-A metal.

21. The process of claim 20, wherein the Group VIII metal is cobalt.

22. The process of claim 20, wherein the Group VI A metal is molybdenum.

23. The process of claim 20, wherein the oxide of metal is pre-treated at 600–1000° F. in the presence of organic sulfide.

24. The process of claim 17, wherein the hydrodealkylation is conducted in the presence of a catalyst composition comprising at least a metal selected from the group consisting of noble metal, nickel, combination thereof, and a synthetic zeolite characterized by a X-ray diffraction pattern including inter planar d-spacing (A)

12.36±0.4

11.03±0.2

8.83±0.14

6.18±0.12

6.00±0.10

4.06±0.07

3.91±0.07

3.42±0.06.

25. The process of claim 1, wherein the alkylating is conducted in the presence of a catalyst composition comprising a synthetic zeolite characterized by an X-ray diffraction pattern including inter planar d-spacing (A)

12.36±0.4

11.03±0.2

8.83±0.14

6.18±0.12

6.00±0.10

4.06±0.07

3.91±0.07

3.42±0.06.

26. The process of claim 1, wherein the alkylating agent for the alkylating is methanol or dimethylether.

* * * * *